US00PP25859P3

(12) United States Plant Patent
Mazzardis

(10) Patent No.: US PP25,859 P3
(45) Date of Patent: Sep. 8, 2015

(54) BLUEBERRY PLANT, 'EB 8-1'

(50) Latin Name: ***Vaccinium* hybrid**
Varietal Denomination: EB 8-1

(71) Applicant: Vincent David Mazzardis, Joondalup (AU)

(72) Inventor: Vincent David Mazzardis, Joondalup (AU)

(73) Assignee: PRUNUS PERSICA PTY LTD, Joondalup (AU)

( * ) Notice: Subject to any disclaimer, the term of this patent is extended or adjusted under 35 U.S.C. 154(b) by 153 days.

(21) Appl. No.: 13/986,863

(22) Filed: Jun. 12, 2013

(65) Prior Publication Data

US 2013/0340131 P1 Dec. 19, 2013

(30) Foreign Application Priority Data

Jun. 14, 2012 (AU) ..... 2012/116

(51) Int. Cl.
*A01H 5/00* (2006.01)
*A01H 5/08* (2006.01)

(52) U.S. Cl.
USPC ..... Plt./157
CPC ..... *A01H 5/08* (2013.01)

(58) Field of Classification Search
USPC ..... Plt./157
See application file for complete search history.

(56) References Cited

FOREIGN PATENT DOCUMENTS

AU PBR 2012/116 6/2012

*Primary Examiner* — Annette Para
(74) *Attorney, Agent, or Firm* — Paine Hamblen, LLP

(57) ABSTRACT

A new and distinct variety of blueberry plant, which is denominated varietally as 'EB 8-1' and which produces a large fruit, which is mature for harvesting and shipment in the early season under the ecological conditions prevailing in Yanchep Springs, Western Australia.

1 Drawing Sheet

Latin name: '*Vaccinium* Hybrid'.
Varietal denomination: 'EB 8-1'.

RELATED APPLICATION DATA

The present application claims priority to Australian Plant Breeders Rights application Serial No. 2012/116, and which was filed on 14 Jun. 2012.

BACKGROUND OF THE NEW VARIETY

The present invention relates to a new, novel, and distinct variety of blueberry plant '*Vaccinium* Hybrid,' and which has been denominated varietally, hereinafter, as 'EB 8-1'.

ORIGIN

The present variety of blueberry resulted from an ongoing development program which I've conducted to identify such plants. The purpose of this program is to improve the commercial quality of blueberry plants and other species. To this end, I have made controlled hybrid cross-pollinations in order to produce plant populations from which improved progeny are evaluated and thereafter selected.

The blueberry plant 'EB 8-1' was originated by me and selected from a population of new plants growing at my farm, which is located near Yanchep Springs, in Yanchep, Western Australia. The new variety of plant was derived from a controlled cross-pollination of the seed parent, blueberry plant '03-6' [unpatented], and a pollen parent, blueberry plant '99-41' [unpatented] during the 2005 growing season. The seed parent blueberry plant '03-6' [unpatented] is principally characterized by a semi-spreading growth habit, and which further has an early season for flowering. Still further, the fruit produced by the seed parent is medium to large in size in relative comparison to other varieties. On the other hand, the pollen parent, blueberry plant '99-41' is characterized by a spreading growth habit and an early season of flowering in relative comparison to other varieties. Additionally, the pollen parent produces relatively large sized fruit. The resulting seed derived from the seed parent, as noted above, produced approximately 500 plants. The fruit of these new plants were assessed in 2007. A further assessment was conducted in 2008. At that time, the new variety 'EB 8-1' was selected for further propagation. Further asexual reproduction of the new variety 'EB 8-1' has led to the conclusion that it is a distinct and new variety of blueberry plant. Additional vegetative propagation has occurred during the 2009 through 2011 growing seasons. The present new variety of blueberry plant is considered to be novel in view of its production of extra large sized fruit, and which further has a small, dry picking scar. Additionally, the new blueberry plant has a very good fruit flavor and produces early flowers. Still further, the fruit of the new variety is ripe for harvesting at a date earlier in the season in relative comparison to other known varieties.

In comparison to the seed parent blueberry plant '03-6,' the present, new variety of blueberry plant, produces fruit which will mature for harvesting and shipment early in the growing season, under the ecological conditions prevailing in Yanchep, Western Australia. This date of maturity is before the date of maturity of the seed parent '03-6,' and which is mature for harvesting and shipment in the early to mid-season, under the ecological conditions prevailing in Yanchep, Western Australia. Still further, the new variety of blueberry plant produces fruit having a size, which is considered very large in relative comparison to the medium sized fruit produced by the seed parent blueberry plant '03-6.' Furthermore, the new variety of blueberry plant has a growth habit which is considered to be spreading in relative comparison to the bushy to spreading growth pattern as typically displayed by the seed parent blueberry plant '03-6.' Moreover, the new blueberry plant produces fruit which are clearly distinguishable from that of the seed parent. The new and novel blueberry plant has a fruit shape, which is considered to be flattened, and globose as opposed to the globose shape of the fruit produced by the seed parent '03-6.'

In relative comparison to the pollen parent, that being blueberry plant '99-41,' the pollen parent produces fruit which are ripe for harvesting and shipment in the mid to late season, under the ecological conditions prevailing in Yanchep, Western Australia. As noted above, the new and novel variety of blueberry plant is ripe for harvesting and shipment in the early season, under the ecological conditions existing in Yanchep, Western Australia. In comparison to the pollen parent, which produces small to medium sized fruit, the new and novel blueberry plant, as described herein, produces very large fruit under the growing conditions prevailing in Yanchep, Western Australia. Again, as noted above, the growth habit of the new variety of blueberry plant is spreading. This is in contrast to the growth habit of the pollen parent, blueberry plant '99-41,' which has an upright growth habit. Again, the fruit shape of the new and novel blueberry plant is considered flattened, and globose. This is in contrast to the fruit shape of the pollen parent, blueberry '99-41' [unpatented] and which produces fruit which are globose in shape.

The present, and new and novel variety of blueberry plant 'EB 8-1' is distinguishable from the most closely related variety, which is the 'Sharpeblue' blueberry plant [unpatented]. In this regard, the 'Sharpeblue' blueberry plant is well known, and is widely grown by both commercial growers and homeowners. The 'Sharpeblue' blueberry plant produces fruit which are ripe for harvesting and shipment early to mid season and further has a fruit size which is considered to be medium in relative comparison to other varieties. Still further, the 'Sharpeblue' blueberry plant has a bushy to spreading growth pattern and a fruit shape which is considered to be globose. In contrast, the new variety is ripe for harvesting and shipment early in the season, and further produces fruit having a very large fruit size. Additionally, the new variety of blueberry plant has a spreading growth pattern, and further the fruit shape is considered to be flattened and globose. The asexual propagation of the present plant was accomplished by means of cuttings. My observations of the new and novel plant over a number of years has confirmed the characteristics of the present variety across these multiple generations.

BRIEF DESCRIPTION OF THE DRAWINGS

The accompanying drawing which is provided is a color photograph of the new blueberry plant.

FIG. 1 illustrates the new variety of blueberry plant 'EB 8-1' and shows a portion of a vegetative stem showing the growth habit of the leaves; several leaves are further illustrated showing the dorsal and ventral coloration, thereof, and the relative sizes of several fruit are depicted showing both the dorsal and ventral coloration, and morphology of same. FIG. 1 additionally shows a vegetative stem, leaves, and fruit produced by the closest known variety, that being the 'Sharpeblue' blueberry plant.

The color in this photograph is as nearly true as is possible in a color representation of this type. Due to chemical development processing and printing, the leaves and fruit depicted in this photograph may or may not be accurate when compared to the actual specimen. For this reason, future color references should be made to the color plates as provided by The Royal Horticulture Society Colour Charts ($5^{th}$ Edition), and other color descriptions provided hereinafter. Common color names are also employed, hereinafter.

NOT A COMMERCIAL WARRANTY

The following detailed descriptions were prepared to solely comply with the provisions of 35 U.S.C. §112, and does not constitute a commercial warranty (either expressed or implied) that the present variety will, in the future, display the botanical, horticultural or other characteristics as set forth, hereinafter. Therefore, this disclosure may not be relied upon to support any future legal claims including, but not limited to, breach of warranty of merchantability, or fitness for any particular purpose, or non-infringement, which is directed, in whole, or in part, to the present new variety.

PLANT

Plant vigor: Generally considered medium for the species. This is in contrast to the closest known variety 'Sharpeblue,' and wherein the plant vigor is considered medium to strong.

Plant growth habit: Generally speaking, considered spreading. This is in contrast to the closest known variety, as indicated above, and which has an upright growth pattern.

*Plant size*.—About 1.2 meters high; and about 1.2 meters in width.

One year old shoots:

*Color*.—Yellow-Green, this color appears indistinguishable from the closest known variety (RHS 151A).

One year old shoots: Internode Length — Considered medium to long.

LEAF

Leaf length: Generally considered to be medium for the species, about 61 mm. In relative comparison to the closest known variety, that being the 'Sharpeblue' blueberry plant, the closest known variety has medium to long leaves. This is best seen by reference to FIG. 1 where the side-by-side leaf comparisons show that the leaf sizes are quite distinct.

Leaf width: Generally considered medium for the species, about 32 mm. This is in contrast to the leaves produced by the 'Sharpeblue' blueberry plant which are medium to broad. This is best seen by reference to FIG. 1.

Leaf ratio (length/width): Considered average for the species. This is in contrast to the leaves produced by the 'Sharpeblue' blueberry plant which are considered medium to large.

Leaf shape: Generally, ovate. Please see FIG. 1 for a comparison of the leaves of the present variety and that of the closet known variety, noted above.

Leaf color:

*Dorsal surface*.—Green, (RHS 136A).

Leaf color:

*Intensity*.—Dorsal surface — Green (RHS 138B). This is in contrast to the green color as seen on the 'Sharpeblue' blueberry plant where this same coloration is considered to be light to medium. This can best be seen by reference to FIG. 1.

Leaf margin:

*Generally*.—Entire.

FLOWER

Flower buds:

*Coloration*.—The presence of anthocyanin is considered to be very weak.

*Flower coloration*.—The open flower color is Grey-Green (RHS 192D).

Inflorescence length: Considered medium for the species, about 14 mm.

Average flower width: About 8 mm.

Flower shape: Urceolate.

Flower size:

*Corolla*.—Considered medium for the species. Average Corolla Length — about 12 mm. This is in contrast to the closest known variety where the corolla size is considered medium to large.

Coloration of corolla tube: Generally speaking a very weak to weak anthocyanin color is present. This is in contrast to the closest known variety 'Sharpeblue' where the anthocyanin coloration is considered merely weak.

Corolla ridges: Present.

FRUIT

Fruit cluster density: Considered medium for the species. This is in contrast to the same characteristic as displayed in the 'Sharpeblue' blueberry plant where this plant displays a fruit cluster density which is considered to be dense.

Unripe fruit:

*Color*.—Generally speaking the unripe fruit of the present variety is yellow-green in color (RHS N144C), and is further considered to have an average color intensity. This is in contrast to the fruit produced by the 'Sharpeblue' blueberry plant where the intensity of the green coloration is considered to be light to medium.

Fruit size:

*Generally*.—Considered large for the species, about 21 mm. This is in relative comparison to the medium sized fruit produced by the 'Sharpeblue' blueberry plant. This is clearly seen by reference to FIG. 1, where the contrast in relative fruit sizes is quite evident.

Longitudinal sectional fruit shape:

*Generally*.—Oblate.

Sepal position: Considered erect to semi-erect. This is in contrast to the sepals as displayed by the 'Sharpeblue' blueberry plant where the sepals assume an erect orientation.

Sepal form: Considered straight.

Calyx diameter: Generally considered medium to large, about 6.2 mm. This is in contrast to the calyx diameter display by the 'Sharpeblue' blueberry plant, which is considered small to medium.

Calyx basin/depth: Considered medium for the species, about 3 mm.

Fruit:

*Bloom intensity*.—Considered strong for the species.

Fruit coloration at full maturity: Considered black (RHS 203D);

Color of fruit flesh: Yellow-Green (RHS 145A).

Fruit firmness: Considered medium. This is in contrast to the fruit produced by the 'Sharpeblue' blueberry plant, which is considered soft to medium for the species.

Color of seeds: Brown (RHS 200C).

Fruit sweetness: Considered medium for the species.

Fruit acidity: Considered average for the species.

Plant fruiting: Typically occurs on one year old, and current season's shoots.

Vegetative bud burst: Considered very early for the species. This is in contrast to the same displayed characteristic in the 'Sharpeblue' blueberry plant where the bud burst is considered just merely early.

Time of flowering: One year old shoots — Considered very early for the species. This is in contrast to the early time of flowering on one year old shoots of the 'Sharpeblue' blueberry plant.

Date for the flowering on current year's shoots: Considered very early for the species. This is in contrast to the closest known variety where this date is only merely considered early in relative comparison to other varieties.

Date of fruit ripening on one year old shoots: Considered very early in contrast to the closest known variety where the date of fruit ripening is only considered early to medium for that species.

Date of ripening of fruit on current year's shoots: Considered very early for the species.

Resistance to insects and disease: No particular susceptibilities were noted. The present variety has not been tested to expose or detect any susceptibilities or resistances to any known plant and/or fruit diseases.

Although the new variety of blueberry plant possesses the described characteristics when grown under the ecological conditions prevailing near Yanchep, Western Australia, it should be understood that the variations of the usual magnitude and characteristics incident to changes in growing conditions, fertilization, pruning, pest control, frost, climatic variables and horticultural management are to be expected.

Having thus described and illustrated my new variety of blueberry plant, what I claim is new and desire to secure by Plant Letters Patent is:

1. A new and distinct variety of blueberry plant, substantially as illustrated and described and which is characterized as to novelty by producing a relatively large fruit, which is mature for harvesting and shipment in the very early season under the ecological conditions prevailing near Yanchep Springs, Western Australia.

* * * * *

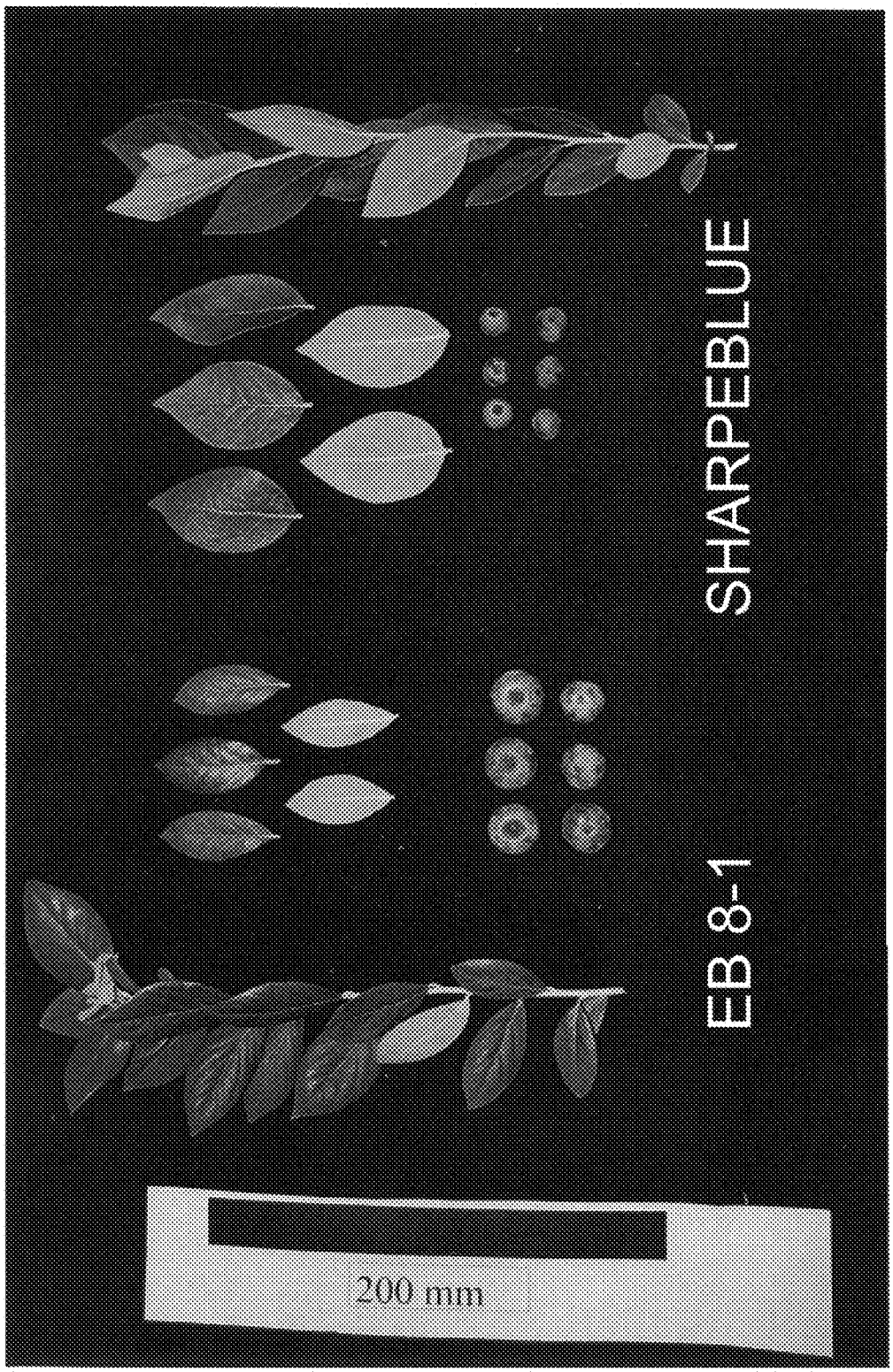
EB 8-1
SHARPEBLUE
200 mm